US00PP22796P2

(12) United States Plant Patent
Hennebelle et al.

(10) Patent No.: US PP22,796 P2
(45) Date of Patent: Jun. 19, 2012

(54) ***BERBERIS* PLANT NAMED 'LUTIN ROUGE'**

(50) Latin Name: *Berberis thungergii*
Varietal Denomination: Lutin Rouge

(76) Inventors: Jean-Loup Hennebelle, Rue de Marais (FR); Nicolas Hennebelle, Rue de Marais (FR)

( * ) Notice: Subject to any disclaimer, the term of this patent is extended or adjusted under 35 U.S.C. 154(b) by 0 days.

(21) Appl. No.: 13/373,895

(22) Filed: Dec. 5, 2011

(51) Int. Cl.
*A01H 5/00* (2006.01)

(52) U.S. Cl. ..... Plt./241

(58) Field of Classification Search ..... Plt./241
See application file for complete search history.

*Primary Examiner* — Annette Para
(74) *Attorney, Agent, or Firm* — Penny J. Aguirre

(57) ABSTRACT

A new cultivar of *Berberis*, 'Lutin Rouge', that is characterized by its oval plant habit, its leaves that are bright red in color, and its non-flowering habit.

2 Drawing Sheets

Botanical classification: *Berberis thungergii*.
Cultivar designation: 'Lutin Rouge'.

BACKGROUND OF THE INVENTION

The present invention relates to a new and distinct cultivar of *Berberis thungerii*, and will be referred to hereafter by its cultivar name, 'Lutin Rouge'. 'Lutin Rouge' is grown for use as a landscape shrub.

The new cultivar was discovered by the Inventors as a whole plant mutation in a garden in 1998 in Boubers sur Canche, France. The parent plants are unknown.

Asexual reproduction of the new cultivar was first accomplished by one the Inventors stem cuttings in Boubers sur Canche, France in 2001. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Lutin Rouge' as a new and distinct cultivar of *Berberis*.

1. 'Lutin Rouge' exhibits an oval plant habit.
2. 'Lutin Rouge' exhibits leaves that are bright red in color.
3. 'Lutin Rouge' is non-flowering.

'Lutin Rouge' can be most closely compared to the cultivar 'Admiration' (U.S. Plant Pat. No. 16,921). 'Admiration' differs from 'Lutin Rouge' in having slightly larger leaves that are red-orange in color with thin yellow-green margins when young and in having young stems that darker red-orange in color. 'Lutin Rouge' can also be compared to the cultivars 'FIREBALL' (U.S. Plant Pat. No. 21,100) and 'ROSY ROCKET' (U.S. Plant Pat. No. 18,413). Both cultivars are similar to 'Lutin Rouge' in having red foliage. 'FIREBALL' differs from 'Lutin Rouge' primarily in having a semi-prostrate plant habit and 'ROSY ROCKET' differs primarily in having an upright columnar plant habit.

BRIEF DESCRIPTION OF THE DRAWING

The accompanying colored photographs illustrate the overall appearance and distinct characteristics of the new *Berberis*. The photographs were taken of a plant about three years in age as grown outdoors in a garden in Gien, France.

The photograph in FIG. 1 provides a view of the plant habit of 'Lutin Rouge' and the photograph in FIG. 2 provides a close-up view of the foliage of 'Lutin Rouge'. The colors in the photographs may differ slightly from the color values cited in the detailed botanical description, which accurately describe the colors of the new *Berberis*.

DETAILED BOTANICAL DESCRIPTION OF THE PLANT

Figure 1:
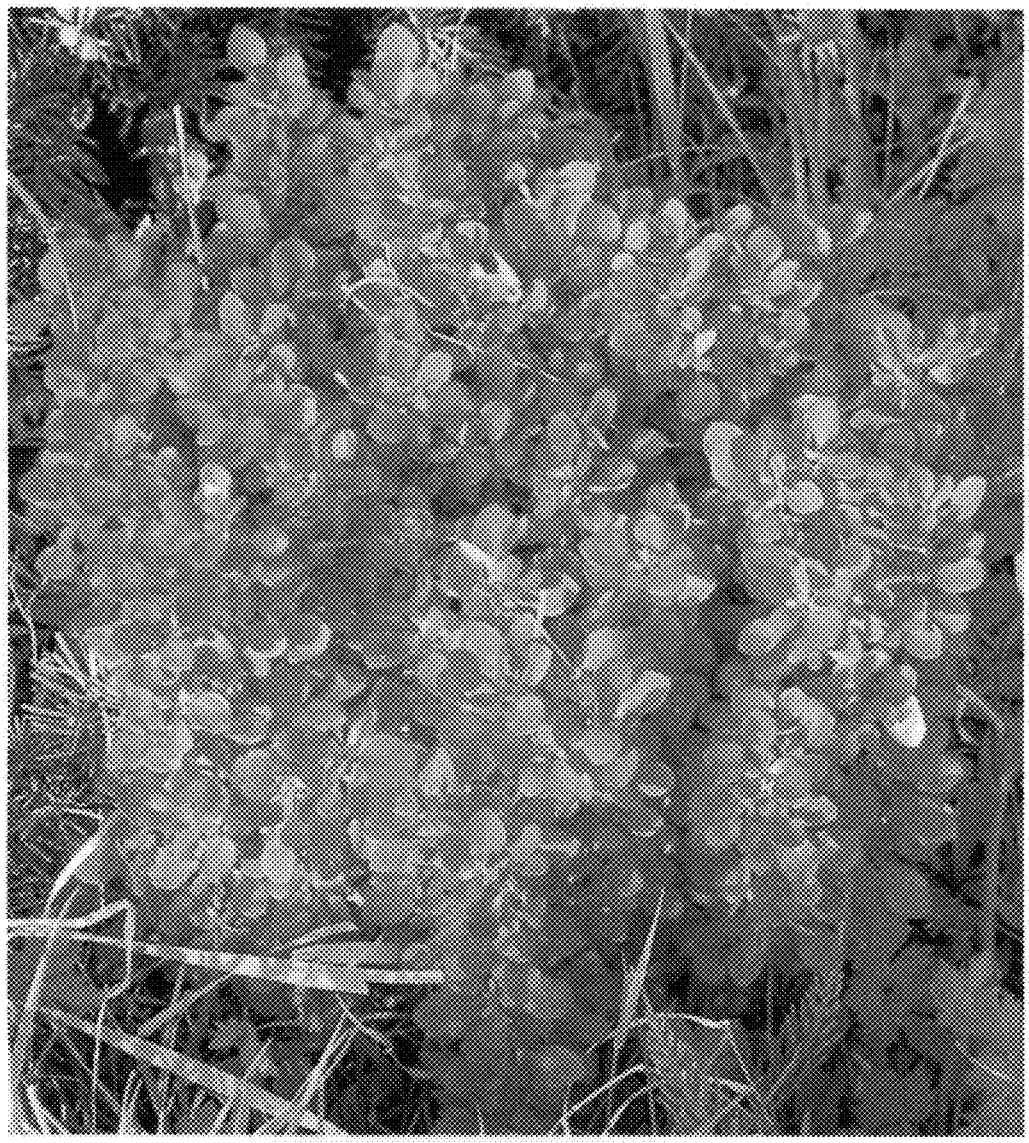
Figure 2:
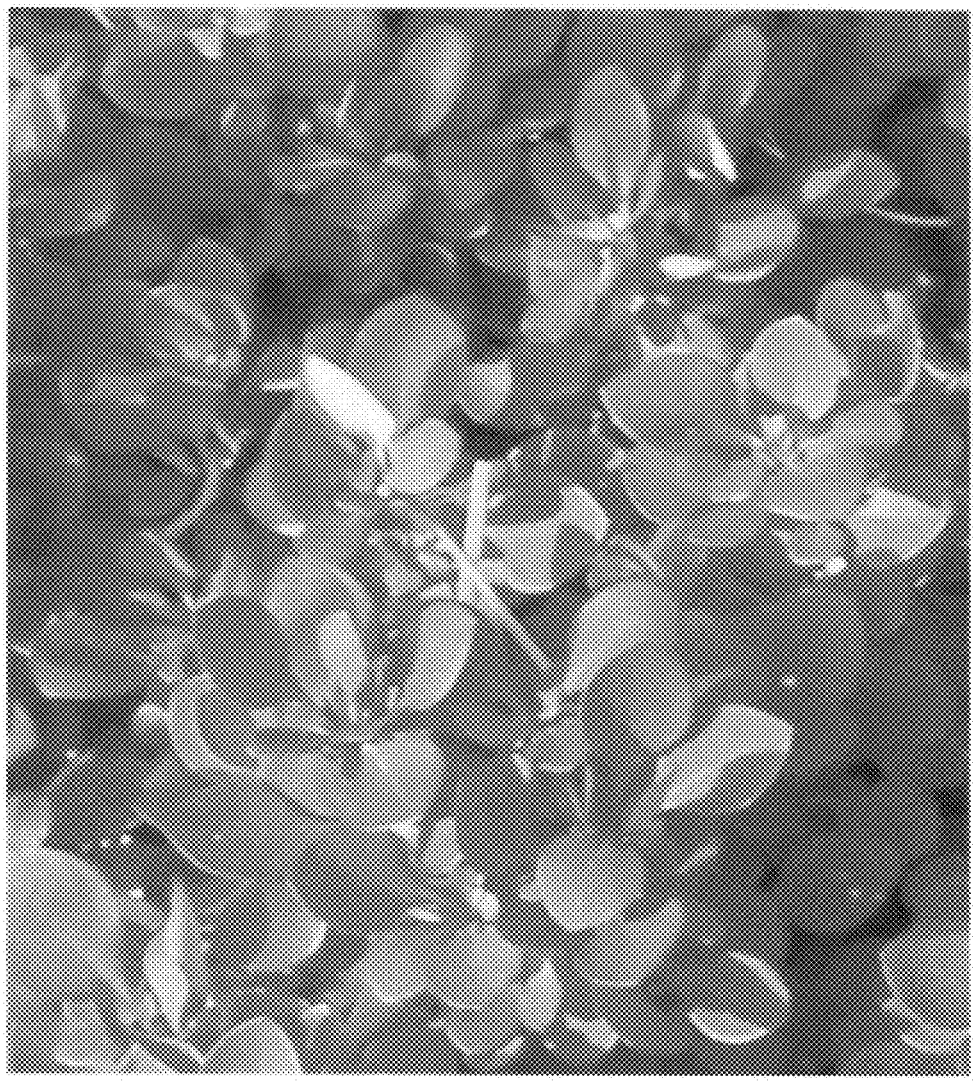

The following is a detailed description of three-year-old plants of the new cultivar field grown outdoors in Gien, France. Plants were grown under average day temperatures of 12° to 32° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Perennial deciduous shrub.

*Plant habit*.—Broad upright spreading.

*Height and spread*.—Reaches about 46 cm in height and 61 cm in width in a 1.5 liter container.

*Hardiness*.—Tolerates temperatures to 35° C. and is hardy to at least U.S.D.A. Zone 5.

*Disease resistance*.—No particular resistance to diseases has been observed.

*Root description*.—Fibrous.

*Growth rate*.—Moderate, about 7 cm in one season on a young plant.

*Propagation*.—Terminal stem cuttings.

Stem description:

*Stem size*.—Lateral branches are an average of 9.2 cm in length and 2 mm in width.

*Stem shape*.—Round.

*Stem color*.—Young shoots; 171A to 171B, later turning 153A to 153B, mature stems; a color between N199C and 200D with darker stripes 200B and 200C.

*Stem surface*.—Young stems; slightly glossy, mature stems; slightly glossy and slightly axially ribbed.

*Stem strength*.—Strong.

*Internode length*.—Average of 7 mm.

*Branching habit*.—Moderate to high with an average of 98 lateral branches.

*Branching aspect*.—Main branches; broad spreading in an average of 90°, lateral branches straight upright in an average angle of 90°.

Foliage description:

*Leaf shape*.—Elliptic to obovate.

*Leaf division*.—Simple.

*Leaf base*.—Long attenuate.

*Leaf apex*.—Rounded to broadly acute.

*Leaf venation*.—Pinnate.

*Leaf margins*.—Entire.

*Leaf attachment*.—Sessile.

*Leaf arrangement*.—Alternate.

*Leaf surface*.—Smooth to moderately glossy on upper and lower surface.

*Leaf color*.—Upper surface immature foliage; 179A, lower surface immature foliage; 180B to 180C changing to 182C to 182D, mature foliage upper surface; from 183A to 183B with older shaded leaves at base of branch 143B to 143C flushed with 183D, mature lower surface foliage; 148C to 148D flushed with 182D, with older shaded leaves at base of branch 146C to 146D.

*Leaf number*.—Average of 14 per lateral branch.

*Leaf size*.—Average of 1.7 cm in length and 1.1 cm in width.

*Leaf aspect*.—Held upward at about a 45° angle.

*Leaf fragrance*.—None.

*Leaf veins*.—Upper surface; from 174B to 174C, on older shaded leaves at base of branch range from 144B to 144C, lower surface; range from 144B to 144C, on older shaded leaves at base of branch range 144A to 144B.

*Petioles*.—Average of 7 mm in length and 0.7 mm in width, 175B to 175C in color and 144A in color on older shaded leaves at base of branch.

*Thorn*.—Below each node is a sharp single thorn; average of 6 mm length at base and 1 mm average width at base, 151C to 151D in color and 200A at tip.

Flower description:

*Flowering*.—No flowers have been observed.

*Fruit and seed*.—Seed production has not been observed.

It is claimed:

1. A new and distinct cultivar of *Berberis* plant named 'Lutin Rouge' as herein illustrated and described.

* * * * *